United States Patent [19]
Takase et al.

[11] Patent Number: 5,627,284
[45] Date of Patent: May 6, 1997

[54] PROCESS FOR PRODUCING (E)-ALKOXYIMINO OR HYDROXYIMINOACETAMIDE COMPOUNDS AND INTERMEDIATES THEREFOR

[75] Inventors: Akira Takase, Otsu; Hiroyuki Kai, Yamatokoriyama; Moriyasu Masui, Yokkaichi; Kuniyoshi Nishida, Shiga-ken, all of Japan

[73] Assignee: Shionogi & Co., Ltd., Osaka, Japan

[21] Appl. No.: 433,931

[22] Filed: May 2, 1995

Related U.S. Application Data

[62] Division of Ser. No. 144,425, Nov. 2, 1993, Pat. No. 5,442,063.

[30] Foreign Application Priority Data

Nov. 2, 1992 [JP] Japan ..................... 4-294225
Dec. 3, 1992 [JP] Japan ..................... 4-324120

[51] Int. Cl.$^6$ .................................. C07D 213/62
[52] U.S. Cl. ................. 546/300; 558/410; 564/197; 568/631
[58] Field of Search ............ 546/300; 558/410; 568/631; 564/197

[56] References Cited

FOREIGN PATENT DOCUMENTS

| 0009865 | 4/1980 | European Pat. Off. . |
|---|---|---|
| 0132124 | 1/1985 | European Pat. Off. . |
| 0477631 | 4/1992 | European Pat. Off. . |
| 0528337 | 2/1993 | European Pat. Off. . |
| WO89/12629 | 12/1989 | WIPO . |
| WO93/17013 | 9/1993 | WIPO . |

*Primary Examiner*—Amelia A. Owens
*Attorney, Agent, or Firm*—Wenderoth, Lind & Ponack

[57] ABSTRACT

The present invention relates to a process for producing (E)-alkoxyiminoacetamide compounds useful as agricultural fungicides and a process for producing (E)-hydroxyiminoacetamide compounds useful as intermediates for producing them. The present invention also relates to an industrial process for producing (E)-methoxyiminoacetamide compounds useful as agricultural fungicides. This process is advantageous in terms of the cost, safety and the like.

13 Claims, No Drawings

PROCESS FOR PRODUCING (E)-ALKOXYIMINO OR HYDROXYIMINOACETAMIDE COMPOUNDS AND INTERMEDIATES THEREFOR

This application is a division of application Ser. No. 08/144,425, filed Nov. 2, 1993 (now U.S. Pat. No. 5,442,063).

FIELD OF THE INVENTION

The present invention relates to a process for producing (E)-alkoxyiminoacetamide compounds useful as agricultural fungicides and a process for producing (E)-hydroxyiminoacetamide compounds useful as intermediates for producing the (E)-alkoxyiminoacetamide compounds. The present invention also relates to novel intermediate compounds for the processes.

BACKGROUND OF THE INVENTION

Attention has been paid to certain kinds of alkoxyiminoacetamide compounds because of their excellent fungicidal activities against microorganisms such as *Pyricularia oryzae*, *Rhizoctonia solani*, *Pseudoperonospora cubensis* and the like. Several compounds of them and processes for their production are known (JP-A 63-23852, JP-A 63-30463).

The present applicant has filed patent applications on the processes for producing alkoxyiminoacetamide compounds, particularly methoxyiminoacetamide compounds (JP-A 3-246268, JP-A 4-89464, JP-A 4-182461, JP-A 5-97768, Japanese Patent Application No. 3-334858, etc.).

However, there is still room for improvement in these processes in terms of the cost, safety and the like of the raw materials and reagents to be used. There is still a need for an economical process for producing them using safe raw materials and reagents.

Further, alkoxyiminoacetamde compounds exist as E- or Z-isomers due to the configuration of the imino group. Since the E-isomers have more potent fungicidal activities, there is a need for processes giving the E-isomers in high ratio and high yield.

OBJECTS OF THE INVENTION

The main object of the present invention is to provide a novel process for producing (E)-alkoxyiminoacetamide compounds or (E)-hydroxyiminoacetamide compounds.

Another object of the present invention is to provide a novel process for producing (E)-methoxyimino-N-methylacetamide.

These objects as well as other objects and advantages of the present invention will become apparent from the following description.

SUMMARY OF THE INVENTION

Under these circumstances, the present inventors have intensively studied an efficient industrial process for producing (E)-alkoxyiminoacetamide compounds and (E)-hydroxy-iminoacetamide compounds useful as the intermediates for the production. As a result, it has been found that an (E)-alkoxy (or hydroxy) iminoacetamide can be obtained in high yield by treating the Z-isomer or a mixture of the E- and Z-isomers of the alkoxy (or hydroxy) iminoacetamide with an acid or an acid addition salt of an organic base in a solvent. Thus, the present invention has been completed.

That is, according to the present invention, there is provided a process for producing a compound of the formula (II-1):

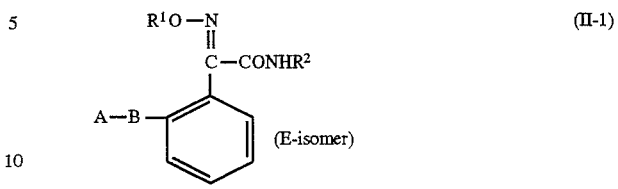

wherein A is hydrogen, alkyl, alkenyl, alkynyl, alkoxy, cycloalkyl, cycloalkenyl, optionally substituted phenyl or an optionally substituted heterocyclic group; B is $-CH_2-$, $-O-$, $-S-$, $-CH(OH)-$, $-CO-$, $-NR^3-$ (wherein $R^3$ is hydrogen or lower alkyl), $-CH_2CH_2-$, $-CH=CH-$, $-C\equiv C-$, $-CH_2O-$, $-CH_2S-$, $-CH_2SO-$, $-OCH_2-$, $-SCH_2-$, $-SOCH_2-$ or epoxy; and $R^1$ and $R^2$ are identically or differently hydrogen or lower alkyl; which comprises treating a compound of the formula (I-1):

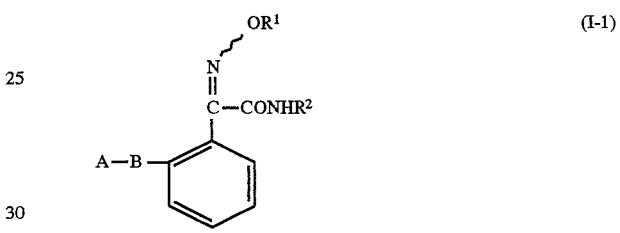

wherein ~ represents any configuration of the Z-isomer or a mixture of the E- and Z-isomers and other symbols are as defined above, with an acid or an acid addition salt of an organic base, provided that, when $R^2$ is lower alkyl, this process is carried out in the presence of a hydrocarbon, halogenated hydrocarbon, ether, ketone or mixed solvent thereof.

DETAILED DESCRIPTION OF THE INVENTION

The present invention also provides the above process for producing a compound of the formula (II-1) which is carried out in the presence of a hydrocarbon, halogenated hydrocarbon, ether, ketone or mixed solvent thereof by using a compound of the formula (I-1) wherein A is hydrogen, optionally substituted phenyl or an optionally substituted heterocyclic group; B is $-CH_2-$, $-O-$, $-S-$, $-CH(OH)-$, $-CO-$, $-NR^3-$ (wherein $R^3$ is hydrogen or lower alkyl), $-CH_2CH_2-$, $-CH=CH-$, $-C\equiv C-$, $-CH_2O-$, $-CH_2S-$, $-CH_2SO-$, $OCH_2-$, $-SOCH_2-$ or and $R^1$ and $R^2$ are identically or differently hydrogen or lower alkyl.

By the term "lower" used in the definitions of the formulae in the present specification is meant having not more than 8 carbon atoms, preferably not more than 6 carbon atoms, more preferably not more than 4 carbon atoms unless otherwise indicated.

The lower alkyl represented by $R^1$, $R^2$ and $R^3$ in the formulae (I-1) and (II-1) includes alkyl having 1 to 6 carbon atoms, preferably 1 to 4 carbon atoms, for example, methyl, ethyl, propyl, isopropyl, butyl, isobutyl, tert-butyl and the like.

As the groups represented by A in the formulae (I-1) and (II-1), there are the following groups.

Examples of the alkyl represented by A include alkyl having 1 to 6 carbon atoms, preferably 1 to 4 carbon atoms, for example, methyl, ethyl, propyl, isopropyl, butyl, isobutyl, tert-butyl and the like.

Examples of the alkenyl represented by A include alkenyl having 2 to 6 carbon atoms, preferably 2 to 4 carbon atoms, for example, vinyl, allyl, crotyl and the like.

Examples of the alkynyl represented by A include alkynyl having 2 to 6 carbon atoms, preferably 2 to 4 carbon atoms, for example, propargyl, ethynyl, butynyl and the like.

Examples of the alkoxy represented by A include alkoxy having 1 to 6 carbon atoms, preferably 1 to 4 carbon atoms, for example, methoxy, ethoxy, propoxy, isopropoxy and the like.

Examples of the cycloalkyl represented by A include cycloalkyl having 3 to 8 carbon atoms, preferably 3 to 6 carbon atoms, for example, cyclopropyl, cyclopentyl, cyclohexyl and the like.

Examples of the cycloalkenyl represented by A include cycloalkenyl having 3 to 8 carbon atoms, preferably 3 to 6 cycloalkenyl, for example, cyclopentenyl, cyclohexenyl and the like.

Examples of the heterocyclic group of the optionally substituted heterocyclic group include 5 to 6 membered heterocyclic groups containing in the ring at least one heteroatom selected from oxygen, sulfur and nitrogen, which may form condensed ring systems with carbocyclic rings or other heterocyclic rings. Examples of the heterocyclic group include pyridyl, pyrimidinyl, pyrazinyl, thiazolyl, benzothiazolyl, benzofuranyl, benzothienyl, oxazolyl, benzoxazolyl, isoxazolyl, pyrazolyl, imidazolyl, quinolyl and the like.

As examples of the substituent of the optionally substituted phenyl or optionally substituted heterocyclic group represented by A, there are lower alkyl (e.g., methyl, ethyl, propyl, butyl, etc.), lower alkenyl (e.g., vinyl, allyl, crotyl, etc.), lower alkynyl (e.g., ethynyl, propargyl, butynyl, etc.), cycloalkyl (e.g., cyclopropyl, cyclopentyl, cyclohexyl, etc.), cycloalkenyl (e.g., cyclopentenyl, cyclohexenyl, etc.), lower alkanoyl (e.g., acetyl, propionyl, isobutyryl, etc.), lower alkylsilyl (e.g., methylsilyl ethylsilyl, propylsilyl, butylsilyl, etc.), halogenated alkyl (e.g., chloromethyl, 2-bromoethyl, 1,2-dichloropropyl, etc.), di(lower)alkylamino (e.g., dimethylamino, diethylamino, etc.), phenyl, phenyl(lower) alkyl (e.g., benzyl, phenylethyl, etc.), phenyl(lower)alkenyl (e.g., styryl, cinnamyl, etc.), furyl(lower)alkyl (e.g., 3-furylmethyl, 2-furylethyl, etc.), furyl(lower)alkenyl (e.g., 3-furylvinyl, 2-furylallyl, etc.), halogen (e.g., fluorine, chlorine, bromine, iodine), nitro, cyano, —$OR^4$ [wherein $R^4$ is hydrogen, lower alkyl (e.g., methyl, ethyl, propyl, etc.), lower alkenyl (e.g., vinyl, allyl, crotyl, etc.), lower alkynyl (e.g., ethynyl, 2-propynyl, 3-butynyl, etc.), lower alkanoyl (e.g., acetyl, propionyl, butyryl, etc.), phenyl, lower alkoxyphenyl (e.g., 3-methoxyphenyl, 4-ethoxyphenyl, etc.), nitrophenyl (e.g., 3-nitrophenyl, 4-nitrophenyl, etc.), phenyl (lower)alkyl (e.g., benzyl, phenylethyl, phenylpropyl, etc.), cyanophenyl(lower)alkyl (e.g., 3-cyanophenylmethyl, 4-cyanophenylethyl, etc.), benzoyl, tetrahydropyranyl, pyridyl, trifluoromethylpyridyl, pyrimidinyl, benzothiazolyl, quinolyl, benzoyl(lower)alkyl (e.g., benzoylmethyl, benzoylethyl, etc.), benzenesulfonyl or lower alkylbenzenesulfonyl (e.g., toluenesulfonyl, etc.)] and —$CH_2$—Z—$R^5$ [wherein Z is —O—, —S— or —$NR^3$— (wherein $R^3$ is as defined above), $R^5$ is phenyl, halophenyl (e.g., 2-chlorophenyl, 4-fluorophenyl, etc.), lower alkoxyphenyl (e.g., 2-methoxyphenyl, 4-ethoxyphenyl, etc.), pyridyl or pyrimidinyl], or phenyl or heterocyclic groups optionally substituted with these substituents.

These substituents of the phenyl or heterocyclic group represented by A may be at any possible position on the ring and may be the same or different. The number of the substituents is preferably 1 to 3.

The compound (I-1) may be any of its Z-isomer or mixtures of the E- and Z-isomers. This is indicated by the wave line (~) in the formula (I-1).

As the acid in the present invention, hydrohalogenic acids, hydrogen halides and sulfonic acids are preferably used. Examples of the hydrohalogenic acid include hydrochloric acid, hydrobromic acid, hydroiodic acid and the like. Examples of the hydrogen halide include hydrogen chloride, hydrogen bromide, hydrogen iodide and the like. Examples of the sulfonic acids include aliphatic sulfonic acids (e.g., trifluoromethanesulfonic acid, etc.), aromatic sulfonic acids (e.g., toluenesulfonic acid, etc.) and the like. Among them, hydrochloric acid, hydrobromic acid, hydrogen chloride gas, hydrogen bromide gas and toluenesulfonic acid are particularly preferred for the object of the invention. The amount of the acid to be used in the invention is 0.005 to 20 mol, preferably 0.05 to 3 mol per mol of the compound (I-1).

As the acid addition salt of an organic base in the present invention, hydrohalogenic acid addition salts of organic bases are preferably used. Examples of the hydrohalogenic acid include hydrochloric acid, hydrobromic acid and the like. As the organic base, any organic base can be used so long as it is capable of forming hydrohalogenic acid addition salts. Examples of the organic base include aliphatic amines (e.g., methylamine, triethylamine. etc.), alkoxyamines, hydroxylamine, aromatic carbocyclic amines (e.g., aniline, etc.) and heterocyclic amines (e.g., pyridine, etc.). Among these acid addition salts of organic bases, hydrochloric acid addition salts of pyridine or aniline are particularly preferred for the object of the invention. The amount of the acid addition salts of organic bases to be used is 0.05 to 20 mol, preferably 0.3 to 3 mol per mol of the compound (I-1).

As the solvent in the invention, hydrocarbons, halogenated hydrocarbons, ethers or ketones, or mixed solvents thereof are preferably used. Examples of the hydrocarbons include benzene, toluene, xylene and the like. Examples of the halogenated hydrocarbons include methylene chloride, 1,2-dichloroethane and the like. Examples of the ethers include tetrahydrofuran, dioxane and the like. Examples of the ketones include acetone, methyl ethyl ketone and the like. Among them, toluene, methylene chloride, dioxane and acetone are particularly preferred for the object of the invention. The amount of the solvent to be used is 1 to 50 times (by weight) that of the compound (I-1).

The reaction temperature is 0° to 180° C., preferably 20° to 140° C. The reaction time is 10 minutes to 200 hours, preferably 30 minutes to 150 hours.

The (E)-alkoxy (or hydroxy)iminoacetamide (II-1) thus obtained can be used as agricultural fungicides, for example, according to the method described in JP-A 3-246268, if necessary, after treatments such as alkylation (e.g., methylation, etc.) by known methods.

The compound (I-1) used as the raw material in the invention can be obtained, for example, according to the method described in JP-A 3-246268. The crude compound (I-1) can also be used as the raw material in the invention. For example, as shown in the following scheme, α-ketoamide (V) is reacted with hydroxylamine or methoxylamine by conventional methods to give the compound (I-1), followed by isomerization of the resulting compound (I-1) by the process of the invention to give the compound (II-1) with the high E-isomer content.

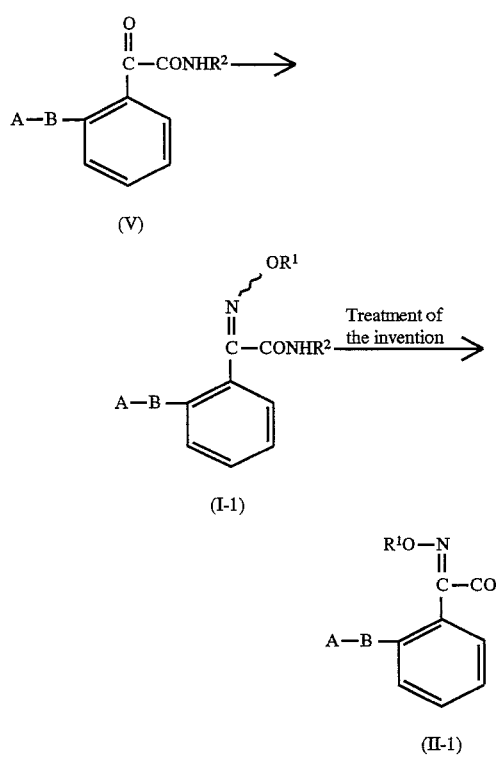

wherein each symbol is as defined above. The crude product (I-1) used as the raw material in the invention is not limited to that obtained by the above method, and any crude compound (I-1) formed by processes giving the compound (I-1) can be used for the process (isomerization) of the invention.

In another aspect of the present invention, the present inventors have intensively studied an industrial process for producing (E)-methoxyiminoacetamide compounds which is an advantageous process in terms of the cost and safety. As a result, it has been found that the desired (E)-methoxyimino-N-methylacetamide (the compound (III) in Scheme hereinafter) can be obtained in high yield by (i) obtaining a mixture of the E- and Z-isomers (the compounds (I-3) and (I-4) in Scheme 1) by using as an intermediate for the production a benzyl halide (the compound (VI-1) in Scheme 1) which can be readily derived from a commercially available cheap raw material, (ii) treating the mixture of the E- and Z-isomers with an acid or an acid addition salt of an organic base for isomerization to obtain the E-isomer, and (iii) methylating the E-isomer.

That is, according to the present invention, there is also provided a process for producing a compound of the formula (III):

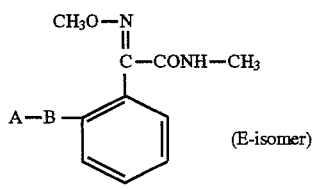

wherein A is hydrogen, alkyl, alkenyl, alkynyl, alkoxy, cycloalkyl, cycloalkenyl, optionally substituted phenyl or an optionally substituted heterocyclic group; and B is —CH$_2$—, —O—, —S—, —CH(OH)—, —CO—, —NR$^3$— (wherein R$^3$ is hydrogen or lower alkyl), —CH$_2$CH$_2$—, —CH=CH—, —C≡C—, —CH$_2$O—, —CH$_2$S—, —CH$_2$SO$_2$SO—, —OCH$_2$—, —SCH$_2$—, —SOCH$_2$— or epoxy; which comprises treating a compound of the formula (I-2):

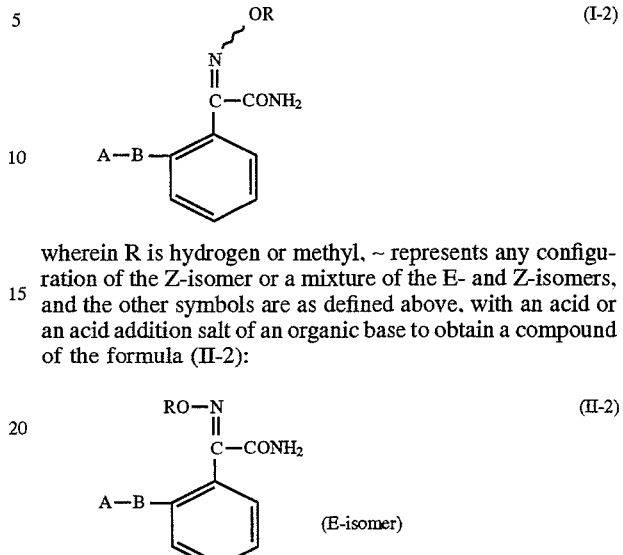

wherein R is hydrogen or methyl, ~ represents any configuration of the Z-isomer or a mixture of the E- and Z-isomers, and the other symbols are as defined above, with an acid or an acid addition salt of an organic base to obtain a compound of the formula (II-2):

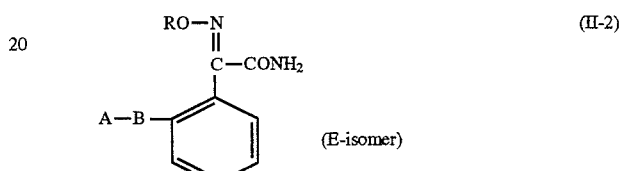

wherein each symbol is as defined above, and then methylating the compound of the formula (II-2).

The present invention also provides the above process for producing a compound of the formula (III) wherein the compound of the formula (I-2) is obtained by hydrolyzing a compound of the formula (IV-1):

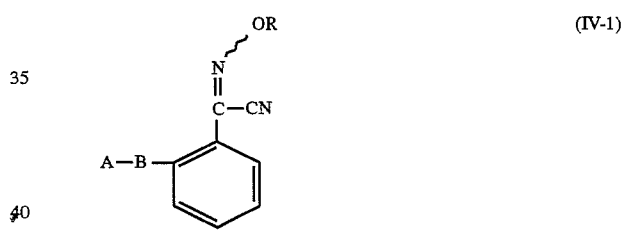

wherein each symbol is as defined above.

The present invention also provides the above process for producing a compound of the formula (III) wherein the compound of the formula (IV-1) is obtained by reacting a compound of the formula (VI-1):

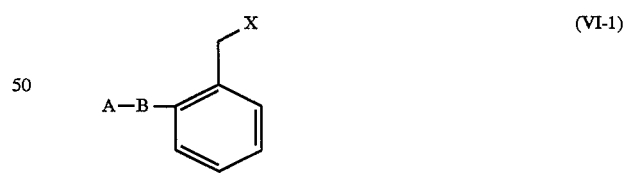

wherein X is halogen and the other symbols are as defined above, with an alkaline metal cyanide to obtain a compound of the formula (V-1):

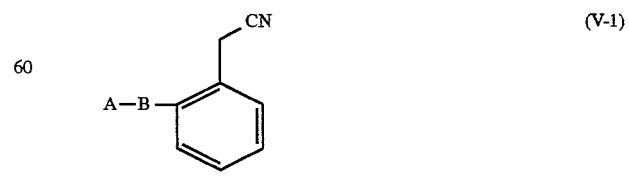

wherein each symbol is as defined above, forming an oxime from the compound of the formula (V-1), and then, if necessary, methylating the oxime.

The present invention also provides a process for producing a compound of the formula (XII):

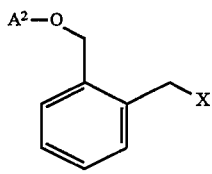

wherein $A^2$ is alkyl, alkenyl, alkynyl, alkoxy, cycloalkyl, cycloalkenyl, optionally substituted phenyl or an optionally substituted heterocyclic group, and X is halogen, which comprises reacting a compound of the formula (X):

                                    (X)

wherein $A^2$ is as defined above, with a comound of the formula (XI):

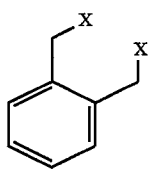                                    (XI)

wherein X is as defined above. The present invention also provides a process for producing a compound of the formula (III) by using the compound of the formula (XII) obtained from the compounds of the formulae (XI) and (X) by the above process.

Further, the present invention also provides the following novel compounds usuful as intermediates for the process of the invention:

a compound of the formula (VI-2):

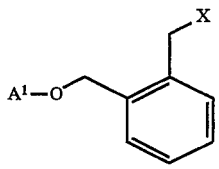                                    (VI-2)

wherein X is halogen and $A^1$ is substituted phenyl or an optionally substituted heterocyclic group;

a compound of the formula (V-2):

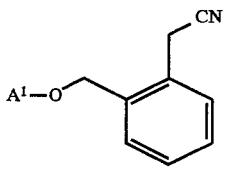                                    (V-2)

wherein $A^1$ is as defined above; and a compound of the formula (IV-2):

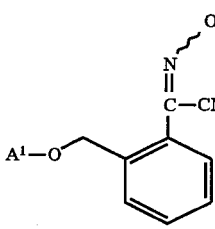                                    (IV-2)

wherein $A^1$ is as defined above.

As examples of each group represented by A or B in the formulae (I-2), (II-2), (III), (IV-1), (V-1) and (VI-1), there are the same groups as those represented by A or B in the formula (I-1).

As examples of the heterocyclic group in the optionally substituted heterocyclic group represented by $A^1$ and its substituent as well as the substituent of the substituted phenyl represented by $A^1$ in the formulae (IV-2), (V-2) and (VI-2), there are the same groups as those described for the heterocyclic group represented by A and its substituent as well as the substituent of the substituted phenyl represented by A. Among them, $A^1$ is preferably 2,5-dimethylphenyl, 2-methylphenyl or optionally substituted pyridyl.

Examples of the halogen represented by X in the formulae (VI-1) and (VI-2) include fluorine, chlorine, bromine and iodine.

In the process of the invention, the methoxyiminoacetamide compounds of the formula (III) can be prepared according to the pathway shown in Scheme 1.

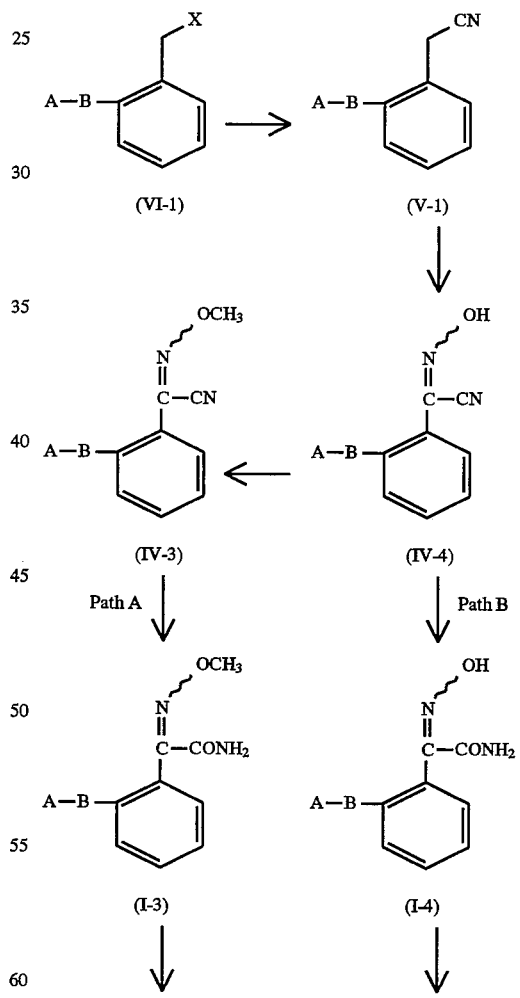

-continued
Scheme 1

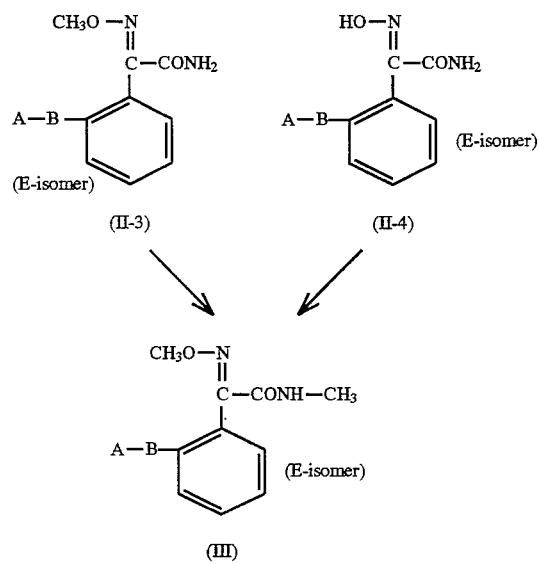

wherein each symbol is as defined above.

Firstly, the benzyl halide (VI-1) is reacted with an alkaline metal cyanide in an appropriate solvent in the presence or absence of a phase-transfer catalyst to obtain the benzyl cyanide (V-1).

Examples of the alkaline metal cyanide to be used include sodium cyanide, potassium cyanide and the like. The amount of the alkaline metal cyanide to be used is 1 to 5 mol, preferably 1 to 2 mol per mol of the benzyl halide (VI-1).

Examples of the solvent to be used include acetone, acetonitrile, methyl ethyl ketone, dimethylformamide (DMF), dimethyl sulfoxide (DMSO), toluene, methanol, ethanol, isopropanol, butanol, tetrahydrofuran (THF), dioxane, water and the like. These solvents can be used alone or in combination thereof.

Examples of the phase-transfer catalyst include tetra-n-butylammonium chloride, tetra-n-butylammonium bromide, tetra-n-butylammmonium hydrogensulfate, tetramethylammmonium bromide, benzyltriethylammonium chloride, tris(3,6-dioxaheptyl)amine and the like. The amount of the phase-transfer catalyst to be used is 0.01 to 0.2 mol, preferably 0.05 to 0.1 mol per mol of the benzyl halide (VI-1).

The reaction temperature is 0° to 120° C., preferably 20° to 100° C. The reaction time is 10 minutes to 24 hours, preferably 30 minutes to 5 hours.

The benzyl cyanide (V-1) thus obtained can be used in the next step as the reaction mixture or the crude product, or after purification by conventional methods.

Then, the above benzyl cyanide (V-1) is reacted with an alkyl nitrite for formation of an oxime in an appropriate solvent in the presence of a base in the presence or absence of a phase-transfer catalyst to obtain α-hydroxyiminobenzyl cyanide (IV-4).

Examples of the alkyl nitrite to be used include methyl nitrite, ethyl nitrite, propyl nitrite, isopropyl nitrite, butyl nitrite, isoamyl nitrite and the like. The amount of the alkyl nitrite to be used is 1 to 5 mol, preferably 1 to 2 mol per mol of the benzyl cyanide (V-1).

Examples of the solvent to be used include the same solvents as those described for the above reaction using the alkaline metal cyanide. These solvent can be used alone or in combination thereof.

Examples of the base to be used include sodium hydroxide, potassium hydroxide, sodium carbonate, potassium carbonate, sodium methoxide, sodium ethoxide, potassium tert-butoxide and the like. The amount of the base to be used is 1 to 5 mol, preferably 1 to 2 mol per mol of the benzyl cyanide (V-1).

Examples of the phase-transfer catalyst include the same phase-transfer catalysts as those described for the above reaction using the alkaline metal cyanide. The amount of the phase-transfer catalyst to be used is 0.01 to 0.2 mol, preferably 0.05 to 0.1 mol per mol of the benzyl cyanide (V-1).

The reaction temperature is 0° to 120° C., preferably 20° to 50° C. The reaction time is 5 minutes to 12 hours, preferably 30 minutes to 3 hours.

The α-hydroxyiminobenzyl cyanide (IV-4) thus obtained can be used in the next step as the reaction mixture or the crude product, or after purification by conventional methods.

The desired (E)-methoxyimino-N-methylacetamide (III) can be obtained from the α-hydroxyiminobenzyl cyanide (IV-4) via the following Path A or Path B.

Path A

The above α-hydroxyiminobenzyl cyanide (IV-4) is reacted with a methylating agent in an appropriate solvent in the presence of a base in the presence or absence of a phase-transfer catalyst to obtain α-methoxyiminobenzyl cyanide (IV-3).

Examples of the methylating agent to be used include dimethyl sulfate, methyl chloride, methyl bromide, methyl iodide and the like. The amount of the methylating agent to be used is 1 to 5 mol, preferably 1 to 2 mol per mol of the α-hydroxyiminobenzyl cyanide (IV-4).

Examples of the base to be used include sodium hydroxide, potassium hydroxide, sodium carbonate, potassium carbonate, sodium methoxide, sodium ethoxide, potassium tert-butoxide and the like. The amount of the base to be used is 1 to 5 mol, preferably 1 to 2 mol per mol of the α-hydroxyiminobenzyl cyanide (IV-4).

Examples of the solvent to be used include the same solvents as those described for the above reaction using the alkaline metal cyanide. These solvents can be used alone or in combination thereof.

Examples of the phase-transfer catalyst include the same phase-transfer catalysts as those described for the above reaction using the alkaline metal cyanide. The amount of the phase-transfer catalyst to be used is 0.01 to 0.2 mol, preferably 0.05 to 0.1 mol per mol of the α-hydroxyiminobenzyl cyanide (IV-4).

The reaction temperature is 0° to t20° C., preferably 0° to 30° C. The reaction time is 5 minutes to 12 hours, preferably 15 minutes to 2 hours.

Alternatively, the benzyl cyanide (V-1) is reacted with an alkyl nitrite under the same conditions as those described for the conversion of the compound (V-1) to the compound (IV-4). Then, a methylating agent is added to the reaction mixture for the methylation. Thus, α-methoxyiminobenzyl cyanide (IV-3) can be obtained by one-pot synthesis.

The α-methoxyiminobenzyl cyanide (IV-3) thus obtined can be used in the next step as the reaction mixture or the crude product, or after purification by conventional methods.

Then, the above α-methoxyiminobenzyl cyanide (IV-3) is hydrolyzed in an appropriate solvent in the presence of a base to obtain the methoxyiminoacetamide (I-3).

Examples of the base to be used include sodium hydroxide, potassium hydroxide, sodium carbonate, potassium carbonate, sodium methoxide, sodium ethoxide, potassium tert-butoxide and the like. The amount of the base to be used is 1 to 20 mol, preferably 1 to 2 mol per mol of the α-methoxyiminobenzyl cyanide (IV-3).

This reaction may be carried out in the presence of hydrogen peroxide. When hydrogen peroxide is used, the amount of the base to be used can be reduced to 0.05 to 1 mol per mol of the α-methoxyiminobenzyl cyanide (IV-3). The amount of the hydrogen peroxide to be used is 1 to 10 mol, preferably 2 to 6 mol per mol of the α-methoxyiminobenzyl cyanide (IV-3).

Examples of the solvent to be used include methanol, ethanol, isopropanol, butanol, toluene, tert-butanol, acetone, methyl ethyl ketone and the like.

The reaction temperature is 20° to 150° C., preferably 50° to 100° C. The reaction time is 10 minutes to 24 hours, preferably 30 minutes to 5 hours.

This reaction may be carried out in the presence of a phase-transfer catalyst. Examples of the phase-transfer catalyst include the same phase-transfer catalysts as those described for the above reaction using the alkaline metal cyanide. The amount of the phase-transfer catalyst to be used is 0.01 to 0.2 mol, preferably 0.05 to 0.1 mol per mol of the α-methoxyiminobenzyl cyanide (IV-3).

The methoxyiminoacetamide (I-3) thus obtained can be used in the next step as the reaction mixture or the crude product, or after purification by conventional methods.

Then, the above methoxyiminoacetamide (I-3) is isomerized in an appropriate solvent in the presence of an acid or an acid addition salt of a base to obtain (E)-methoxyiminoacetamide (II-3).

There is another method giving the desired (E)-methoxyimino-N-methylacetamide (III) from the methoxyiminoacetamide (I-3) wherein the compound (I-3) is firstly reacted with a methylating agent before isomerizing the compound (I-3) and then isomerized. In this method, however, the Z-isomer contained in the methoxyiminoacetamide (I-3) forms a large amount of N,N-dimethylacetamide (VII) shown below as the by-product when methylation is carried out before isomerization. Further, the Z-isomer content in the methoxyiminoacetamide (I-3) is at least 70%. The (E)-methoxyimino-N-methylacetamide (III) obtained by isomerization after methylation therefore has an greately lowered purity.

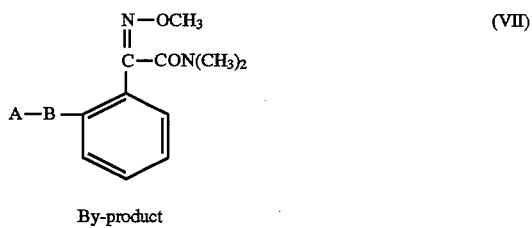

By-product

The (E)-methoxyiminoacetamide (I-3) therefore needs to be firstly isomerized to give the (E)-methoxyiminoacetamide (II-3).

The isomerization of the methoxyiminoacetamide (I-3) can be carried out by the process of isomerization of the invention described above. That is, as the acid, there can preferably be used hydrohalogenic acids, hydrogen halides, sulfonic acids and acid addition salts of organic bases.

Examples of the hydrohalogenic acids include hydrochloric acid, hydrobromic acid, hydroiodic acid and the like. Examples of the hydrogen halides include hydrogen chloride, hydrogen bromide, hydrogen iodide and the like. Examples of the sulfonic acids include aliphatic sulfonic acids (e.g., trifluoromethanesulfonic acid, etc.), aromatic sulfonic acids (e.g., toluenesulfonic acid, etc.) and the like.

As the acid addition salts of organic bases, hydrohalogenic acid addition salts of organic bases are preferably used. Examples of the hydrohalogenic acid include hydrochloric acid, hydrobromic acid and the like. As the organic bases, there can be used any organic base capable of forming hydrohalogenic acid addition salts, for example aliphatic amines (e.g., methylamine, triethylamine, etc.), alkoxyamines, hydroxylamine, aromatic carbocyclic amines (e.g., aniline, etc.), heterocyclic amines (e.g., pyridine, etc.).

The amount of the acid or acid addition salt of organic base to be used is 0.005 to 20 mol, preferably 0.05 to 3 mol per mol of the methoxyiminoacetamide (I-3).

As the solvent, there can preferably be used hydrocarbons, halogenated hydrocarbons, ethers or ketones, or mixtures thereof. Examples of the hydrocarbons include benzene, toluene, xylene and the like. Examples of the halogenated hydrocarbons include methylene chloride, 1,2-dichloroethane and the like. Examples of the ethers include tetrahydrofuran, dioxane and the like. Examples of the ketones include acetone, methyl ethyl ketone and the like. The amount of the solvent is about 1 to 50 times (by weight) that of the methoxyiminoacetamide (I-3).

The reaction temperature is 0° to 180° C., preferably 20° to 140° C. The reaction time is 10 minutes to 200 hours, preferably 30 minutes to 150 hours.

The (E)-methoxyiminoacetamide (II-3) thus obtained can be used in the next step as the reaction mixture or the crude product, or after purification by conventional methods.

Then, the above (E)-methoxyiminoacetamide (II-3) is reacted with a methylating agent in an appropriate solvent in the presence of a base in the presence or absence of a phase-transfer catalyst to obtain the desired (E)-methoxyimino-N-methylacetamide (III).

Examples of the methylating agent to be used include dimethyl sulfate, methyl chloride, methyl bromide, methyl iodide and the like. The amount of the methylating agent to be used is 1 to 5 mol, preferably 1 to 2 mol per mol of (E)-methoxyiminoacetamide (II-3).

Examples of the base to be used include sodium hydroxide, potassium hydroxide, sodium carbonate, potassium carbonate, sodium methoxide, sodium ethoxide, potassium tert-butoxide and the like. The amount of the base to be used is 1 to 5 mol, preferably 1 to 2 mol per mol of (E)-methoxyiminoacetamide (II-3).

Examples of the solvent include the same solvents as those described for the above reaction using the alkaline metal cyanide. These solvents can be used alone or in combination thereof.

Examples of the phase-transfer catalyst include the same phase-transfer catalysts as those described for the above reaction using alkaline metal cyanide. The amount of the phase-transfer catalyst to be used is 0.01 to 0.2 mol, preferably 0.05 to 0.1 mol per mol of the (E)-methoxyiminoacetamide (II-3).

The reaction temperature is 0° to 140° C., preferably 0° to 100° C. The reaction time is 10 minutes to 12 hours, preferably 20 minutes to 6 hours.

Path B

The α-hydroxyiminobenzyl cyanide (IV-4) obtained above is reacted with a base in an appropriate solvent in the presence or absence of a phase-transfer catalyst to obtain the hydroxyiminoacetamide (I-4).

Examples of the base to be used include sodium hydroxide, potassium hydroxide, sodium carbonate, potassium carbonate, sodium methoxide, sodium ethoxide, potassium tert-butoxide and the like. The amount of the base to be used is 1 to 30 mol, preferably 2 to 20 mol per mol of the α-hydroxyiminobenzyl cyanide (IV-4).

Examples of the solvent to be used include methanol, ethanol, isopropanol, butanol, toluene, tert-butanol and the like.

Examples of the phase-transfer catalyst include the same phase-transfer catalysts as those described for the above reaction using the alkaline metal cyanide. The amount of the phase-transfer catalyst to be used is 0.01 to 1 mol, preferably 0.01 to 0.1 mol per mol of the α-hydroxyiminobenzyl cyanide (IV-4).

The reaction temperature is 20° to 150° C., preferably 50° to 120° C. The reaction time is 30 minutes to 24 hours, preferably 1 to 12 hours.

The hydroxyiminoacetamide (I-4) thus obtained can be used in the next step as the reaction mixture or the crude product, or after purification by conventional methods.

Then, the above hydroxyiminoacetamide (I-4) is isomerized in an appropriate solvent in the presence of an acid or an acid addition salt of an organic base to obtain (E)-hydroxyiminoacetamide (II-4).

There is another method giving the desired (E)-methoxyimino-N-methylacetamide (III) from the hydroxyiminoacetamide (I-4) wherein the compound (I-4) is firstly reacted with a methylating agent before isomerizing the compound (I-4) and then isomerized. In this method, however, the Z-isomer contained in the hydroxyiminoacetamide (I-4) forms various by-products when methylation is carried out before isomerization. Among them, two kinds of nitrons (VIII) and (IX) shown below are formed in large amounts. Further, the Z-isomer content in most of the hydroxyiminoacetamides (I-4) is at least 70% The (E)-methoxyimino-N-methylacetamide (III) obtained by isomerization after methylation therefore has an greatly lowered purity.

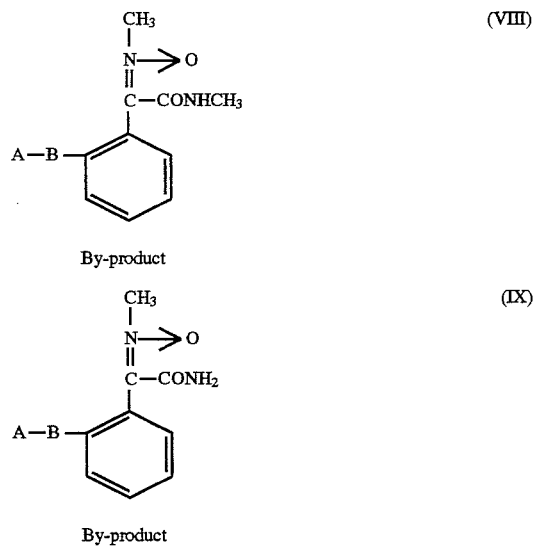

By-product (VIII)

By-product (IX)

The (E)-hydroxyiminoacetamide (I-4) therefore needs to be firstly isomerized to give the (E)-hydroxyiminoacetamide (II-4).

The isomerization of the hydroxyiminoacetamide (I-4) can be carried out by the process of isomerization of the invention described above. That is, as the acid, there can preferably be used hydrohalogenic acids, hydrogen halides, sulfonic acids and acid addition salts of organic bases.

Examples of the hydrohalogenic acids include hydrochloric acid, hydrobromic acid, hydroiodic acid and the like. Examples of the hydrogen halides include hydrogen chloride, hydrogen bromide, hydrogen iodide and the like. Examples of the sulfonic acids include aliphatic sulfonic acids (e.g., trifluoromethanesulfonic acid, etc.), aromatic sulfonic acids (e.g., toluenesulfonic acid, etc.) and the like.

As the acid addition salts of organic bases, hydrohalogenic acid addition salts of organic bases are preferably used. Examples of the hydrohalogenic acid include hydrochloric acid, hydrobromic acid and the like. As the organic bases, there can be used any organic base capable of forming hydrohalogenic acid addition salts, for example aliphatic amines (e.g., methylamine, triethylamine, etc.), alkoxyamines, hydroxylamine, aromatic carbocyclic amines (e.g., aniline, etc.), heterocyclic amines (e.g., pyridine, etc.).

The amount of the acid or acid addition salt of organic base to be used is 0.005 to 20 mol, preferably 0.05 to 3 mol per mol of the hydroxyiminoacetamide (I-4).

As the solvent, there can preferably be used hydrocarbons, halogenated hydrocarbons, ethers or ketones, or mixtures thereof. Examples of the hydrocarbons include benzene, toluene, xylene and the like. Examples of the halogenated hydrocarbons include methylene chloride, 1,2-dichloroethane and the like. Examples of the ethers include tetrahydrofuran, dioxane and the like. Examples of the ketones include acetone, methyl ethyl ketone and the like. The amount of the solvent is about 1 to 50 times (by weight) that of the hydroxyiminoacetamide (I-4).

The reaction temperature is 0° to 180° C., preferably 20° to 140° C. The reaction time is 10 minutes to 200 hours, preferably 30 minutes to 150 hours.

The (E)-hydroxyiminoacetamide (II-4) thus obtained can be used in the next step as the reaction mixture or the crude product, or after purification by conventional methods.

Then, the resulting (E)-hydroxyiminoacetamide (II-4) is reacted with a methylating agent in an appropriate solvent in the presence of a base to obtain the desired (E)-methoxyimino-N-methylacetamide (III).

Examples of the methylating agent to be used include dimethyl sulfate, methyl chloride, methyl bromide, methyl iodide and the like. The amount of the methylating agent to be used is 2 to 10 mol, preferably 2 to 3 mol per mol of (E)-hydroxyiminoacetamide (II-4).

Examples of the base to be used include sodium hydroxide, potassium hydroxide, sodium carbonate, potassium carbonate, sodium methoxide, sodium ethoxide, potassium tert-butoxide and the like. The amount of the base to be used is 2 to 10 mol, preferably 2 to 3 mol per mol of (E)-hydroxyiminoacetamide (II-4).

Examples of the solvent to be used include the same solvents as those described for the above reaction using the alkaline metal cyanide. These solvents can be used alone or in combination thereof.

The reation temperature is 0° to 140° C., preferably 0° to 100° C. The reaction time is 10 minutes to 5 hours, preferably 30 minutes to 2 hours.

The (E)-methoxyimino-N-methylacetamide (III) thus obtained can be used as agricultural fungicides, for example, by the method described in JP-A 3-246268, if necessary, after purification by conventional separation and purification methods such as chromatography and the like.

The benzyl halide (VI-1) used as the starting material in the above process can be prepared, for example, according to the process shown in Scheme 2 when A is other than hydrogen.

Scheme 2 wherein A² is alkyl, alkenyl, alkynyl, alkoxy, cycloalkyl, cycloalkenyl, optionally substituted phenyl or an optionally substituted heterocyclic group, and X is halogen. Examples of each group represented by A² include the same groups as those represented by A in the formula (II-1). A² is preferably optionally substituted phenyl or an optionally substituted heterocyclic group.

The compound (X) is reacted with excess α,α'-o-dihalogenoxylene (XI) in an appropriate solvent in the presence of a base in the presence or absence of a phase-transfer catalyst.

Examples of the α,α'-o-dihalogenoxylene (XI) to be used include α,α'-o-dichloroxylene, α,α'-o-dibromoxylene, α,α'-o-diiodoxylene and the like. The amount of the α,α'-o-dihalogenoxylene (XI) to be used is 1 to 10 mol, preferably 3 to 5 mol per mol of the compound (X). When the reaction is carried out without using excess α,α'-o-dihalogenoxylene (XI), the compound (XIII) of the formula:

wherein each symbol is as defined above, is produced in a large amount.

Examples of the solvent to be used include the same solvents as those described for the above reaction using the alkaline metal cyanide. These solvents can be used alone or in combination thereof.

Examples of the base to be used include sodium hydroxide, potassium hydroxide, sodium carbonate, potassium carbonate, sodium methoxide, sodium ethoxide, potassium tert-butoxide and the like. The amount of the base to be used is 1 to 5 mol, preferably 1 to 2 mol pre mol of the compound (X).

Examples of the phase-transfer catalyst include the same phase-transfer catalysts as those described for the above reaction using the alkaline metal cyanide. The amount of the phase-transfer catalyst to be used is 0.01 to 0.2 mol, preferably 0.05 to 0.1 mol per mol of the compound (X).

The reaction temperature is 0° to 120° C., preferably 20° to 100° C. The reaction time is 20 minutes to 12 hours, preferably 30 minutes to 3 hours.

The remaining α,α'-o-dihalogenoxylene (XI) is removed from the crude benzyl halide (XII) thus obtained. The resulting residue can be used in the next step as it is or after purification by conventional methods.

As described hereinabove, according to the present invention, there is provided a process for producing (E)-alkoxyiminoacetamide compounds useful for agricultural fungicides. There is also provided a process for producing (E)-hydroxyiminoacetamide compounds useful as the intermediate for the above production. These processes of the present invention give the E-isomer in very high ratio and very high yield by isomerization of the Z-isomer or a mixture of the E- and Z-isomer. Further, according to the present invention, there is also provided an industrial process for producing (E)-methoxyiminoacetamide compounds useful as agricultural fungicides. This process is advantageous in terms of the cost, safety and the like.

The following examples further illustrate the present invention in detail but are not to be construed to limit the scope thereof.

EXAMPLE 1

Synthesis of (E)-2-[2-(2,5-dimethylphenoxymethyl)phenyl]-2-hydroxyiminoacetamide Conc. hydrochloric acid (2 ml) and methylene chloride (5 ml) were added to 2-[2-(2,5-dimethylphenoxymethyl)phenyl]-2-hydroxyiminoacetamide (Z=at least 98%) (0.50 g, 1.68 mmol), and the mixture was stirred at room temperature for 15 hours. After stirring, water (5 ml) and toluene (5 ml) were added. The resulting crystals were separated by filtration and dried to give (E)-2-[2-(2,5-dimethylphenoxymethyl)phenyl]-2-hydroxyiminoacetamide (0.48 g, Yield: 96.0%) as colorless crystals.

mp 172°–173° C.

$^1$H-NMR (CDCl$_3$) δ ppm: 2.19(s,3H), 2.29(s,3H), 4.97(s, 2H), 5.38(br.,1H), 6.64–7.74(m,8H).

EXAMPLE 2

Synthesis of (E)-2-[2-(2,5-dimethylphenoxymethyl)phenyl]-2-methoxyiminoacetamide Toluene (4 ml) and conc. hydrochloric acid (0.8 ml) were added to 2-[2-(2,5-dimethylphenoxymethyl)phenyl]-2-methoxyiminoacetamide (E/Z=15/85) (1.25 g, 4.0 mmol), and the mixture was stirred at 85° C. for 2 hours. After the reaction, water (80 ml) was added. The mixture was extracted with toluene (80 ml), dried over anhydrous magnesium sulfate, and concentrated under reduced pressure to give crystals. The crystals were recrystallized from n-hexane/ethyl acetate to give (E)-2-[2-(2,5-dimethylphenoxymethyl)phenyl]-2-methoxyiminoacetamide (1.02 g, Yield: 81.6%) as colorless crystals.

mp 121.5°–122.5° C.

$^1$H-NMR (CDCl$_3$) δ ppm: 2.19(s,3H), 2.29(s,3H), 3.98(s, 3H), 4.93(s,2H), 5.39(br.,1H), 6.61–7.58(m,8H).

EXAMPLE 3

Synthesis of (E)-2-[2-(2,5-dimethylphenoxymethyl)phenyl]-2-methoxyiminoacetamide Methylene chloride (60 ml) and conc. hydrochloric acid (20 ml) were added to 2-[2-(2,5-dimethylphenoxymethyl)phenyl]-2-methoxyiminoacetamide (Z=at least 98%) (6.25 g, 0.02 mol), and the mixture was stirred at room temperature for 18 hours. After completion of the reaction, water (150 ml) was added. The mixture was extracted with methylene chloride (100 ml), dried over anhydrous magnesium sulfate, and concentrated under reduced pressure to give crystals. The crystals were recrystallized from n-hexane/ethyl acetate to give (E)-2-[2-(2,5-dimethylphenoxymethyl)phenyl]-2-methoxyiminoacetamide (5.41 g, Yield: 86.7%) as colorless crystals.

mp 121.5°–122.5° C.

EXAMPLE 4

Synthesis of (E)-2-(2-phenoxyphenyl)-2-hydroxyiminoacetamide

Conc. hydrochloric acid (1 ml) and methylene chloride (12 ml) were added to 2-(2-phenoxyphenyl)-2-hydroxyiminoacetamide (Z=at least 98%) (1.79 g, 7.0 mmol), and the mixture was stirred at room temperature for 12 hours. After stirring, water (20 ml) and toluene (20 ml) were added. The resulting crystals were separated by filtration and dried to give (E)-2-(2-phenoxyphenyl)-2-hydroxyiminoacetamide (1.70 g, Yield: 95.0%) as colorless crystals.

mp 157°–159° C.

$^1$H-NMR (CDCl$_3$) δ ppm: 5.39(br.,1H), 6.58(br.,1H), 6.89–7.39(m,9H), 7.99(s,1H).

EXAMPLE 5

Synthesis of (E)-2-(2-phenoxyphenyl)-2-methoxyiminoacetamide

Toluene (26 ml) and conc. hydrochloric acid (1.1 ml) were added to 2-(2-phenoxyphenyl)-2-methoxyiminoacetamide (E/Z=6/94) (3.48 g, 0.013 mol), and the mixture was stirred at room temperature for 3 hours. After completion of the reaction, water (80 ml) was added. The mixture was extracted with ether (80 ml), dried over anhydrous magnesium sulfate, and concentrated under reduced pressure. The resulting residue was purified by silica gel chromatography (ethyl acetate/n-hexane) to give (E)-2-(2-phenoxyphenyl)-2-methoxyiminoacetamide (3.25 g, Yield: 93.4%).

mp 98°–99° C.

$^1$H-NMR (CDCl$_3$) δ ppm: 3.95(s,3H), 5.28(br.,1H), 6.61 (br.,1H), 6.89–7.37(m,9H).

EXAMPLE 6

Synthesis of (E)-2-(2-phenoxyphenyl)-2-methoxyiminoacetamide 2-(2-phenoxyphenyl)-2-methoxyiminoacetamide (E/Z=24/76) (5.05 g, 18.7 mmol) was dissolved in acetone (19 ml). Conc. hydrochloric acid (1.56 ml) was added, and the mixture was heated under reflux for 3 hours. After completion of the reaction, the reaction mixture was neutralized with a saturated aqueous solution of sodium bicarbonate and extracted with ether. The ether layer was washed with water and saturated brine, dried over anhydrous magnesium sulfate and concentrated under reduced pressure. The resulting residue was purified by silica gel chromatography (ethyl acetate/n-hexane) to give (E)-2-(2-phenoxyphenyl)-2-methoxyiminoacetamide (4.50 g, Yield: 89.1%, E/Z=96/4).

EXAMPLE 7

Synthesis of (E)-2-(2-phenoxyphenyl)-2-methoxyiminoacetamide 2-(2-phenoxyphenyl)-2-methoxyiminoacetamide (E/Z=14/86) (0.27 g, 1 mmol) was dissolved in toluene (1 ml). Conc. hydrochloric acid (0.17 ml) was added, and the mixture was heated at 80° C. for 2 hours. A part of the mixture was sampled, and the toluene was evaporated under reduced pressure to give (E)-2-(2-phenoxyphenyl)-2-methoxyiminoacetamide. The E/Z ratio of it was determined (E/Z=98/2).

EXAMPLE 8

Synthesis of (E)-N-methyl-2-[2-(2,5-dimethylphenoxymethyl)phenyl]-2-methoxyiminoacetamide (Z)-N-methyl-2-[2-(2,5-dimethylphenoxymethyl)phenyl]-2-methoxyiminoacetamide (650 mg, 2 mmol) was dissolved in methylene chloride (4 ml). Conc. hydrochloric acid (0.16 ml) was added, and the mixture was stirred at room temperature for 120 hours. After completion of the reaction, a saturted aqueous solution of sodium bicarbonate (50 ml) was added for neutralization. The resulting mixture was extracted with methylene chloride (100 ml), washed with brine, dried over anhydrous magnesium sulfate and concentrated under reduced pressure to give (E)-N-methyl-2-[2-(2,5-dimethylphenoxymethyl)phenyl]-2-methoxyiminoacetamide (650 mg, Yield: 100%, E/Z=97/3) as colorless crystals.

EXAMPLE 9

Synthesis of (E)-N-methyl-2-(2-phenoxyphenyl)-2methoxyiminoacetamide (Z)-N-Methyl-2-(2-phenoxyphenyl)-2-methoxyiminoacetamide (570 mg, 2 mmol) was dissolved in toluene (10 ml). Hydrobromic acid (47%, 0.52 g) was addd, and the mixture was stirred at room temperature for 3 hours. After completion of the reaction, a saturated aqueous solution of sodium bicarbonate (50 ml) was added for neutralization. The resulting mixture was extracted with methylene chloride (130 ml), washed with brine, dried over anhydrous magnesium sulfate and concentrated under reduced pressure to give (E)-N-methyl-2-(2-phenoxyphenyl)-2-methoxyiminoacetamide (564 mg, Yield: 98.9%, E/Z=96/4).

EXAMPLES 10 TO 21

Isomerization was carried out under various conditions, followed by work up in the same manner as that in Example 9. The results are shown in Table 1.

TABLE 1

| Ex. | (I-1) A—B— | R¹ | R² | E/Z | Acid or base (mol)[1] | Solvent (l/mol) | Reaction condition | | (II-1) E/Z | Yield (%) |
|---|---|---|---|---|---|---|---|---|---|---|
| 10 | 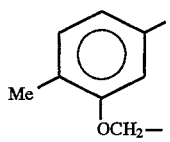 | H | Me | Z | c.HCl[2] (1.0) | $CH_2Cl_2$ (10) | rt[3] | 120 h | 94/6 | 93.5 |
| 11 | " | Me | Me | Z | c.HCl (1.0) | Toluene (4) | reflux | 2 h | 94/6 | 100 |
| 12 | 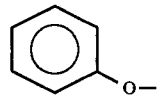 | H | Me | Z | c.HCl (1.0) | $CH_2Cl_2$ (3) | rt | 16 h | 99/1 | 92.6 |
| 13 | " | H | Me | Z | c.HCl (2.0) | Acetone (3) | rt | 5 h | 95/5 | 96.3 |
| 14 | " | Me | Me | Z | HCl gas (1.0) | Dioxane (2) | rt | 3 h | 95/5 | 96.5 |
| 15 | " | Me | Me | Z | 6N HClaq. (2.0) | Toluene (5) | 60° C. | 6 h | 95/5 | 98.2 |
| 16 | 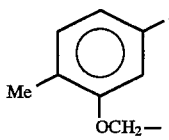 | Me | Me | Z | 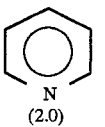 .HCl (2.0) | Toluene (2) $H_2O$ (0.1) | reflux | 16 h | 93/7 | 100 |
| 17 | " | Me | Me | 60/40 | c.HCl (1.0) | Toluene (4) | reflux | 2 h | 94/6 | 93.7 |
| 18 | 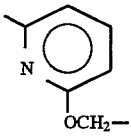 | H | Me | Z | c.HCl (2.0) | Acetone (4) | 60° C. | 20 h | 94/6 | 97.3 |
| 19 | 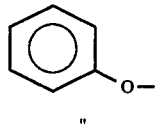 | Me | Me | 57/43 | c.HCl (2.0) | Toluene (4) | reflux | 14 h | 93/7 | 98.3 |
| 20 | 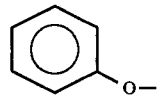 | Me | H | 14/86 | TsOH.$H_2O$ (1.0) | Toluene (1) | 80° C. | 19 h | 94/6 | — |
| 21 | " | Me | Me | Z | 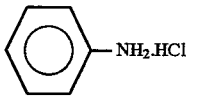 (2.0) | Toluene (2) $H_2O$ (0.3) | reflux | 16.5 h | 94/6 | 99.0 |

Note:
[1] mol is indicated in terms of mol per mol of the compound (I-1).
[2] c.HCl indicates concentrated hydrochloric acid.
[3] rt indicates room temperature.

EXAMPLE 22

Synthesis of (E)-N-methyl-2-[2-(2,5-dimethylphenoxymethyl)phenyl]-2-methoxyiminoacetamide Methyl alcohol (10 ml) and a 50% aqueous solution (1.15 g, 6 mmol) of methoxylamine·½ sulfate were added to N-methyl-2-[2-(2,5-dimethylphenoxymethyl)phenyl]-2-oxoacetamide (1.49 g, 5 mmol). The mixture was refluxed for 6 hours. After completion of the reaction, methyl alcohol was evaporated under reduced pressure. Toluene (10 ml) and conc. hydrochloric acid (1.04 g, 10 mmol) were added to the resulting residue (E/Z=47/53). The mixture was heated at 80° C. for 2 hours. After cooling, toluene (100 ml) was added to the reaction mixture. The mixture was washed with water (100 ml), dried over anhydrous magnesium sulfate and concentrated under reduced pressure. The resulting residue was purified by silica gel chromatography (ethyl acetate/n-hexane) to give (E)-N-methyl-2-[2-(2,5-dimethylphenoxymethyl)phenyl]-2-methoxyiminoacetamide (1.56 g, Yield: 95.5%, E/Z=95/5).

EXAMPLE 23

Synthesis of (E)-N-methyl-2-(2-phenoxyphenyl)-2-hydroxyiminoacetamide

N-Methyl-2-(2-phenoxyphenyl)-2-oxoacetamide (2.55 g, 10 mmol) was dissolved in methyl alcohol (10 ml). Hydroxylamine sulfate (0.99 g, 12 mmol) was added, followed by heating under reflux for 3 hours. After completion of the reaction, methyl alcohol was evaporated under reduced pressure. Toluene (10 ml) and conc. hydrochloric acid (1.04 g) were added to the resulting residue (E/Z=41/59), and the mixture was stirred at room temperature for 20.5 hours. After completion of the reaction, water (300 ml) was added. The mixture was extracted with ethyl acetate (300 ml), washed with brine twice, dried over anhydrous magnesium sulfate and concentrated under reduced pressure to give (E)-N-methyl-2-(2-phenoxyphenyl)-2-hydroxyiminoacetamide (2.58 g, Yield: 95.6%, E/Z=96/4).

EXAMPLE 24

Synthesis of (E)-N-methyl-2-(2-phenoxyphenyl)-2-hydroxyiminoacetamide

Toluene (20 ml) and a 50% aqueous solution (0.71 ml, 12 mmol) of hydroxylamine were added to N-methyl-2-(2-phenoxyphenyl)-2-oxoacetamide (2.55 g, 10 mmol). The mixture was heated under reflux for 4 hours (E/Z=40/60). After cooling, conc. hydrochloric acid (3.0 ml, 30 mmol) was added, and the mixture was stirred at room temperature for 24 hours. After completion of the reaction, the resulting crystals were separated by filtration, washed with water and toluene and dried to give (E)-N-methyl-2-(2-phenoxyphenyl)-2-hydroxyiminoacetamide (2.65 g, Yield: 98.0%, E/Z=98/2).

EXAMPLE 25

Synthesis of (E)-N-methyl-2-[2-(2,5-dimethylphenoxymethyl)phenyl]-2-hydroxyiminoacetamide N-methyl-2-[2-(2,5-dimethylphenoxymethyl)phenyl]-2-oxoacetamide (11.89 g, 0.04 mol) was suspended in methanol (40 ml). Hydroxylamine sulfate (4.92 g, 0.06 mol) was added, and the mixture was refluxed for 8 hours. After completion of the reaction, methanol was evaporated under reduced pressure. The resulting residue (E/Z=46/54) was dissolved in methylene chloride (80 ml), conc. hydrochloric acid (20 ml) was added, and the mixture was stirred at room temperature for 15 hours. Water (50 ml) and toluene (80 ml) were added, and the mixture was stirred at room temperature for 5 minutes. Then the resulting crystals were separated by filtration, washed with water (50 ml) and toluene (50 ml) and dried to give (E)-N-methyl-2-[2-(2,5-dimethylphenoxymethyl)phenyl]-2-hydroxyiminoacetamide (11.32 g, Yield: 90.6%, E/Z=99/1).

Comparative Examples 1 to 5

Isomerization was carried out under the conditions described in JP-A 4-89464. The results are shown in Table 2.

TABLE 2

| Comparative Ex. | (I-1) A—B— | $R^1$ | $R^2$ | E/Z | Acid (mol)[1] | Solvent (l/mol) | Reaction condition | (II-2) E/Z | Yield (%) |
|---|---|---|---|---|---|---|---|---|---|
| 1 | Me—⌬—OCH₂— (with Me substituents) | Me | Me | Z | c.HCl[2] (2.0) | MeOH (2) | reflux 19 h | 46/54 | — |
| 2 | " | Me | Me | Z | 50%H₂SO₄aq. (2.0) | MeOH (2) | reflux 56 h | 76/24 | 97.3 |

Note:
[1] mol is indicated in terms of mol per mol of the compound (I-1).
[2] c.HCl indicates concentrated hydrochloric acid.

EXAMPLE 26-1

Synthesis of 2-(2,5-dimethylphenoxymethyl)benzyl chloride

Potassium carbonate (55.28 g, 0.4 mol), α,α'-o-dichloroxylene (175.06 g, 1.0 mol) and acetone (200 ml) were added to 2,5-xylenol (24.43 g, 0.2 mol). The mixture was heated under reflux for 8 hours. After completion of the reaction, the resulting insoluble materials were removed, and excess α,α'-o-dichloroxylene was evaporated under reduced pressure to obtain 2-(2,5-dimethylphenoxymethyl)benzyl chloride (53.20 g, Yield: 88.5%, Purity: 86.8%) as a colorless oil.

EXAMPLE 26-2

Synthesis of 2-(2,5-dimethylphenoxymethyl)benzyl chloride

95% sodium hydroxide (13.89 g, 0.33 mol) and water (60 ml) were added to 2,5-xylenol (36.65 g, 0.3 mol) and dissolved while heating. Then water was evaporated under reduced pressure. α,α'-o-Dichloroxylene (105.04 g, 0.6 mol) and acetone (150 ml) were added to the resulting sodium salt, and the mixture was heated under reflux for 1 hour. After completion of the reaction, the resulting insoluble materials were removed. After distillation under reduced pressure, 2-(2,5-dimethylphenoxymethyl)benzyl chloride (39.07 g, Yield: 49.9%) was obtained as colorless crystals.

bp 145°–147° C./0.6 mmHg, mp 46.5°–48.5° C.

$^1$H-NMR (CDCl$_3$) δ ppm: 2.21(s,3H), 2.34(s,3H), 4.74(s, 2H), 5.18(s,2H), 6.71–7.54(m,7H).

EXAMPLE 27

Synthesis of 2-(2,5-dimethylphenoxymethyl)benzyl cyanide 2-(2,5-Dimethylphenoxymethyl)benzyl chloride (Purity: 86.8%, 1.50 g, 5 mmol), 95% sodium cyanide (0.31 g, 6 mmol), triethylbenzylammonium chloride (0.06 g, 0.25 mmol), acetone (4 ml) and water (2 ml) were added. The mixture was heated under reflux for 5 hours. After completion of the reaction, water (100 ml) was added. The resulting mixture was extracted with ether (100 ml), dried over anhydrous magnesium sulfate and concentrated under reduced pressure. The resulting residue was purified by silica gel chromatography (ethyl acetate/n-hexane) to give 2-(2,5-dimethylphenoxymethyl)benzyl cyanide (1.23 g, Yield: 97.84).

mp 51.5°–53 ° C.

$^1$H-NMR(CDCl$_3$) δ ppm: 2.18(s,3H), 2.34(s,3H), 3.89(s, 2H), 5.05(s,2H), 6.72–7.52(m,7H).

EXAMPLE 28

Synthesis of 2-(2,5-dimethylphenoxymethyl)-α-hydroxyiminobenzyl cyanide

85% Potassium hydroxide (0.40 g, 6 mmol), toluene (5 ml) and butyl nitrite (0.62 g, 6 mmol) were added to 2-(2,5-dimethylphenoxymethyl)benzyl cyanide (1.26 g, 5 mmol). The mixture was stirred at room temperature for 8 hours. After completion of the reaction, water (100 ml) was added. The mixture was neutralized with hydrochloric acid, extracted with ether (100 ml), dried over anhydrous magnesium sulfate and concentrated under reduced pressure. The resulting residue was purified by silica gel chromatography (ethyl acetate/n-hexane) to give 2-(2,5-dimethylphenoxymethyl)-α-hydroxyiminobenzyl cyanide (1.30 g, Yield: 92.84, E/Z=15/85).

A part of it was taken and separated into the E- and Z-isomers, and the physical properties were determined.

E-isomer:

mp 114°–115° C.

$^1$H-NMR (CDCl$_3$) δ ppm: 2.23 (s,3H), 2.31(s,3H), 5.06 (s,2H), 6.65–7.66(m,7H), 8.41(s,1H).

Z-isomer:

mp 150.5°–151.5° C.

$^1$H-NMR (CDCl$_3$) δ ppm: 2.24(s,3H), 2.31(s,3H), 5.24(s, 2H), 6.64–7.79(m,7H), 8.68(s,1H).

EXAMPLE 29

Synthesis of 2-(2,5-dimethylphenoxymethyl)-α-methoxyiminobenzyl cyanide

Potassium carbonate (3.32 g, 0.024 mol) and acetone (200 ml) were added to 2-(2,5-dimethylphenoxymethyl)-α-hydroxyiminobenzyl cyanide (E/Z=15/85) (5.61 g, 0.02 mol). The mixture was stirred for 5 minutes. Then dimethyl sulfate (3.03 g, 0.024 mol) was added, and the mixture was stirred at room temperature for 18 hours. After completion of the reaction, the resulting insoluble materials were removed. To the residue obtained after evaporation under reduced pressure, toluene (50 ml) and 1N aqueous sodium hydroxide solution (50 ml) were added. The mixture was stirred for 1 hour. After stirring, water (150 ml) was added. The mixture was extracted with ether (150 ml), dried over anhydrous magnesium sulfate and concentrated under reduced pressure. The resulting residue was purified by silica gel chromatography (ethyl acetate/n-hexane) to give 2-(2,5-dimethylphenoxymethyl)-α-methoxyiminobenzyl cyanide (5.44 g, Yield: 92.4%, E/Z=15/85).

A part of it was taken and separated into the E- and Z-isomers, and the physical properties were determined.

E-isomer: Colorless oil.

$^1$H-NMR (CDCl$_3$) δ ppm: 2.23 (s,3H), 2.31(s,3H), 4.04 (s,3H), 5.01(s,2H), 6.63–7.63(m,7H).

Z-isomer: Colorless crystals.

mp 107°–108° C.

$^1$H-NMR (CDCl$_3$) δ ppm: 2.24(s,3H), 2.30(s,3H), 4.13(s, 2H), 5.26(s,2H), 6.62–7.76(m,7H).

EXAMPLE 30

Synthesis of 2-(2,5-dimethylphenoxymethyl)-α-methoxyiminobenzyl cyanide

95% Sodium hydroxide (0.32 g, 7.5 mmol), acetone (5 ml) and butyl nitrite (0.62 g, 6 mmol) were added to 2-(2,5dimethylphenoxymethyl)benzyl cyanide (1.26 g, 5 mmol). The mixture was stirred at room temperature for 2 hours. Dimethyl sulfate (0.95 g, 7.5 mmol) was added, and the mixture was stirred under ice-cooling for 10 minutes and at room temperature for 1 hour. After completion of the reaction, toluene (10 ml) and 1N aqueous sodium hydroxide solution (10 ml) were added, and the mixture was stirred at room temperature for 1 hour. After stirring, water (100 ml) was added. The mixture was extracted with ether (100 ml), dried over anhydrous magnesium sulfate and concentrated under reduced pressure. The resulting residue was purified by silica gel chromatography (ethyl acetate/n-hexane) to give 2-(2,5-dimethylphenoxy-methyl)-α-methoxyiminobenzyl cyanide (1.29 g, Yield: 87.6%, E/Z= 13/87).

EXAMPLE 31

Synthesis of 2-[2-(2,5-dimethylphenoxymethyl)phenyl]-2-hydroxyiminoacetamide

85% Potassium hydroxide (6.12 g, 92.8 mmol) and tert-butyl alcohol (15 ml) were added to 2-(2,5-dimethylphenoxymethyl)-α-hydroxyiminobenzyl cyanide (E/Z=15/85)(1.30 g, 4.64 mmol). The mixture was heated under reflux for 5 hours. After completion of the reaction, the reaction mixture was neutralized with 6N hydrochloric acid, and water (100 ml) was added. The resulting mixture was extracted with ether (100 ml), dried over anhydrous magnesium sulfate and concentrated under reduced pressure. The resulting crystals were recrystallized from n-hexane/ethyl acetate to give 2-[2-(2, 5dimethylphenoxymethyl)phenyl]-2-hydroxyiminoacetamide (0.83 g, Yield: 60.0%, Z=at least 98%) as colorless crystals.

mp 165.5°–167.5° C.

$^1$H-NMR (CDCl$_3$) δ ppm: 2.17(s,3H), 2.31(s,3H), 5.09(s, 2H), 5.70(br.,1H), 5.93(br.,1H), 6.70–7.67(m,7H).

EXAMPLE 32-1

Synthesis of 2-[2-(2,5-dimethylphenoxymethyl)phenyl]-2-methoxyiminoacetamide

85% Potassium hydroxide (0.40 g, 6.0 mmol) and toluene (5 ml) were added to 2-(2,5-dimethylphenoxymethyl)-α-methoxyiminobenzyl cyanide (E/Z=15/85)(1.47 g, 5.0 mmol). The mixture was stirred at 95° C. for 2 hours. After completion of the reaction, water was added. The mixture was neutralized with conc. hydrochloric acid, extracted with toluene (100 ml), dried over anhydrous magnesium sulfate and concentrated under reduced pressure. The resulting residue was purified by silica gel chromatography (ethyl acetate/n-hexane) to give 2-[2-(2,5-dimethylphenoxymethyl)phenyl]-2-methoxyiminoacetamide (1.30 g, Yield: 83.2%, E/Z=15/85).

$^1$H-NMR (CDCl$_3$) δ ppm: 2.19(s,0.45H), 2.20(s,2.55H), 2.29(s,0.45H), 2.30(s,2.55H), 3.98(s,0.45H), 4.05(s, 2.55H), 4.93(s,0.3H), 5.17(s,1.7H), 5.17(br.,0.85H), 5.39(br.,0.15H), 6.61–7.61(m,8H).

EXAMPLE 32-2

Synthesis of 2-[2-(2,5-dimethylphenoxymethyl) phenyl]-2-methoxyiminoacetamide

85% Sodium hydroxide (0.32 g, 6.0 mmol) and toluene (5 ml) were added to 2-[(2,5-dimethylphenoxymethyl)phenyl]-α-methoxyiminobenzyl cyanide (E/Z=15/85) (1.47 g, 5.0 mmol). The mixture was heated under reflux for 2 hours. After completion of the reaction, water (100 ml) was added. The mixture was neutralized with conc. hydrochloric acid, extracted with toluene (100 ml), dried over anhydrous magnesium sulfate and concentrated under reduced pressure. The resulting residue was purified by silica gel chromatography (ethyl acetate/n-hexane) to give 2-[2-(2,5-dimethylphenoxymethyl)phenyl]-2-methoxyiminoacetamide (1.15 g, Yield: 73.6%, E/Z=15/85).

$^1$H-NMR (CDCl$_3$) δ ppm: 2.19(s,0.45H), 2.20(s,2.55H), 2.29(s,0.45H), 2.30(s,2.55H), 3.98 (s,0.45H ), 4.05(s, 2.55H), 4.93(s,0.3H), 5.17(s,1.7H), 5.17(br.,0.85H), 5.39 (br.,0.15H), 6.61–7.61(m, 8H).

EXAMPLE 33

Synthesis of (E)-2-[2-(2,5-dimethylphenoxymethyl) phenyl]-2-methoxyimino-N-methylacetamide Methyl iodide (0.48 g, 3.35 mmol), 85% potassium hydroxide (0.19 g, 2.81 mmol) and toluene (5 ml) were added to (E)-2-[2-(2,5-dimethylphenoxymethyl)phenyl]-2-hydroxyiminoacetamide (0.40 g, 1.34 mmol). The mixture was heated under reflux for 1 hour. After completion of the reaction, water (100 ml) was added. The mixture was extracted with ether (100 ml), dried over anhydrous magnesium sulfate and concentrated under reduced pressure. The resulting crystals were recrystallized from n-hexane/ ethyl acetate to give (E)-2-[2-(2,5-dimethylphenoxymethyl) phenyl]-2-methoxyimino-N-methylacetamide (0.34 g, Yield: 77.7%) as colorless crystals.

mp 136°–137° C.

$^1$H-NMR (CDCl$_3$) δ ppm: 2.18(s,3H), 2.29(s,3H), 2.88 (d,3H,J=4.9 Hz), 3.95(s,3H), 4.92(s,2H), 6.62–7.57(m, 8H).

EXAMPLE 34

Synthesis of (E)-2-[2-(2,5-dimethylphenoxymethyl) phenyl]-2-methoxyimino-N-methylacetamide Methyl chloride (0.45 g, 9.0 mmol), 85% potassium hydroxide (0.30 g, 4.5 mmol) and toluene (9 ml) were added to (E)-2-[2-(2,5-dimethylphenoxymethyl)phenyl]-2-methoxyiminoacetamide (0.94 g, 3.0 mmol). The mixture was stirred at 100° C. for 1 hour. After completion of the reaction, water (100 ml) was added. The mixture was extracted with ether (100 ml), dried over anhydrous magnesium sulfate and concentrated under reduced pressure. The resulting residue was purified by silica gel chromatography (ethyl acetate/n-hexane) to give (E)-2-[2-(2,5-dimethylphenoxymethyl)phenyl]-2-methoxyimino-N-methylacetamide (0.88 g, Yield: 90.2%) as colorless crystals. mp 136°–137° C.

EXAMPLE 35

Synthesis of 2-phenoxy-α-hydroxyiminobenzyl cyanide

854 Potassium hydroxide (3.96 g, 0.06 mol), toluene (100 ml) and butyl nitrite (6.19 g, 0.06 mmol) were added to 2-phenoxybenzyl cyanide (10.46 g, 0.05 mol). The mixture was stirred at room temperature for 16 hours. After completion of the reaction, water (100 ml) was added. The mixture was neutralized with hydrochloric acid, extracted with ether (150 ml), dried over anhydrous magnesium sulfate and concentrated under reduced pressure. The resulting residue was purified by silica gel chromatography (ethyl acetate/n-hexane) to give 2-phenoxy-α-hydroxyiminobenzyl cyanide (11.15 g, Yield: 93.6%, E/Z=11/89).

$^1$H-NMR (CDCl$_3$) δ ppm: 6.91–7.67(m,9H), 8.87(s, 0.1H), 9.33(s,0.9H).

EXAMPLE 36

Synthesis of 2-phenoxy-α-methoxyiminobenzyl cyanide

Potassium carbonate (3.11 g, 0.023 mol) and acetone (60 ml) were added to 2-phenoxy-α-hydroxyiminobenzyl cyanide (E/Z=11/89)(7.15 g, 0.03 mol). The mixture was stirred for 5 minutes. Then dimethyl sulfate (5.68 g, 0.045 mol) was added, and the mixture was stirred at room temperature for 18 hours. After completion of the reaction, the resulting insoluble materials were removed. To the residue obtained after concentration under reduced pressure, toluene (60 ml) and 1N aqueous sodium hydroxide solution (60 ml) were added. The mixture was stirred at room temperature for 1 hour. After stirring, water (60 ml) was added. The mixture was extracted with toluene (100 ml), dried over anhydrous magnesium sulfate and concentrated under reduced pressure. The resulting residue was purified by silica gel chromatography (ethyl acetate/n-hexane) to give 2-phenoxy-α-methoxyiminobenzyl cyanide (6.28 g, Yield: 83.0%, E/Z= 7/93).

$^1$H-NMR (CDCl$_3$) δ ppm: 4.03(s,0.2H), 4.17(s,2.8H), 6.85–7.66(m,9H).

EXAMPLE 37

Synthesis of 2-phenoxy-α-methoxyiminobenzyl cyanide

95% sodium hydroxide (0.40 g, 6 mmol), acetone (10 ml) and butyl nitrite (0.62 g, 6 mmol) were added to 2-phenoxybenzyl cyanide (1.05 g, 5 mmol). The mixture was stirred at room temperature for 1.5 hours. Dimethyl sulfate (0.76 g, 6 mmol) was added, and the mixture was stirred at room temperature for 0.5 hours. After completion of the reaction, ether (10 ml) and 1N aqueous sodium hydroxide solution (10 ml) were added, and the mixture was stirred at room temperature for 0.5 hour. After stirring, water (100 ml) was added. The mixture was extracted with ether (100 ml), dried over anhydrous magnesium sulfate and concentrated under reduced pressure. The resulting residue was purified by silica gel chromatography (ethyl acetate/n-hexane) to give 2-phenoxy-α-methoxyiminobenzyl cyanide (1.18 g, Yield: 93.5%, E/Z=23/77).

$^1$H-NMR (CDCl$_3$) δ ppm: 4.03(s,0.7H), 4.17(s,2.3H), 6.85–7.66(m,9H).

EXAMPLE 38

Synthesis of 2-(2-phenoxyphenyl)-2-hydroxyiminoacetamide

85% Potassium hydroxide (2.57 g, 38.9 mmol) and tert-butyl alcohol (40 ml) were added to 2-phenoxy-α-hydroxyiminobenzyl cyanide (E/Z=11/89)(3.10 g, 13 mmol). The mixture was heated under reflux for 10 hours. After completion of the reaction, the reaction mixture was neutralized with 1N hydrochloric acid, extracted with ethyl acetate (100 ml), dried over anhydrous magnesium sulfate and concentrated under reduced pressure. The resulting crystals were recrystallized from n-hexane/ethyl acetate to give 2-(2-phenoxyphenyl)-2-hydroxyiminoacetamide (2.25 g, Yield: 67.5%, Z=at least 98%) as pale yellow crystals.

mp 188°–190° C.

$^1$H-NMR (CDCl$_3$) δ ppm: 3.60(br.,1H), 6.58(br.,1H), 6.89–7.93(m,9H), 7.99(s,1H).

EXAMPLE 39

Synthesis of 2-(2-phenoxyphenyl)-2-methoxyiminoacetamide

85% Potassium hydroxide (1.19 g, 0.018 mol) and toluene (30 ml) were added to 2-phenoxy-α-methoxyiminobenzyl cyanide (E/Z=7/93)(3.78 g, 0.015 mmol). The mixture was stirred at 80° C. for 2.5 hours. After completion of the reaction, water (100 ml) was added. The mixture was neutralized with conc. hydrochloric acid, extracted with ether (100 ml), dried over anhydrous magnesium sulfate and concentrated under reduced pressure. The resulting residue was purified by silica gel chromatography (ethyl acetate/n-hexane) to give 2-(2-phenoxyphenyl)-2-methoxyiminoacetamide (3.66 g, Yield: 90.3%, E/Z=6/94).

$^1$H-NMR (CDCl$_3$) δ ppm: 3.95(s,0.18H), 4.05(s,2.82H), 5.81(br.,1H), 6.40(br.,1H), 6.84–7.59(m,9H).

EXAMPLE 40

Synthesis of (E)-2-(2-phenoxyphenyl)-2-methoxyimino-N-methylacetamide

Methyl iodide (1.15 g, 8.13 mmol), 85% potassium hydroxide (0.45 g, 6.82 mmol) and toluene (10 ml) were added to (E)-2-(2-phenoxyphenyl)-2-hydroxyiminoacetamide (0.83 g, 3.25 mmol). The mixture was heated under reflux for 0.5 hours. After completion of the reaction, water (100 ml) was added. The mixture was extracted with ether (100 ml), dried over anhydrous magnesium sulfate and concentrated under reduced pressure. The resulting crystals were recrystallized from ethyl acetate/n-hexane to give (E)-2-(2-phenoxyphenyl)-2-methoxyimino-N-methylacetamide (0.54 g, Yield: 58.4%) as colorless crystals.

mp 83°–84° C.

$^1$H-NMR (CDCl$_3$) δ ppm: 2.87(d,3H,J=4.9 Hz), 3.91(s, 3H), 6.65(br.,1H), 6.86–7.36(m,9H).

EXAMPLE 41

Synthesis of (E)-2-(2-phenoxyphenyl)-2-methoxyimino-N-methylacetamide

85% Potassium hydroxide (0.79 g, 12.0 mmol) and toluene (20 ml) were added to (E)-2-(2-phenoxyphenyl)-2-methoxyiminoacetamide (2.70 g, 10.0 mmol) and dissolved by heating to 50° C. After 10 minutes, the solution was concentrated under reduced pressure. Toluene (20 ml) was added to the residue, and dimethyl sulfate (1.32 ml, 14.0 mmol) was added dropwise under ice-cooling and reacted at room temperature for 1 hour. After completion of the reaction, water (100 ml) was added. The mixture was extracted with ether (150 ml), dried over anhydrous magnesium sulfate and concentrated under reduced pressure. The resulting residue was purified by silica gel chromatography (ethyl acetate/n-hexane) to give (E)-2-(2-phenoxyphenyl)-2-methoxyimino-N-methylacetamide (2.33 g, Yield: 82.1%).

mp 83°–84° C.

$^1$H-NMR (CDCl$_3$) δ ppm: 2.87(d,3H,J=4.9 Hz), 3.91(s, 3H), 6.65(br.,1H), 6.86–7.36(m,9H).

EXAMPLE 42

Synthesis of 2-(2-phenoxyphenyl)-2-methoxyiminoacetamide

2-Phenoxy-α-methoxyiminobenzyl cyanide (E/Z=21/79) (1.26 g, 5 mmol) was dissolved in acetone (5 ml). Sodium carbonate (0.11 g, 1 mmol), tetra-n-butylammonium bromide (0.08 g, 0.25 mmol), 30% aqueous hydrogen peroxide solution (1.13 g, 10 mmol) were added, and the mixture was heated under reflux for 5 hours. After completion of the reaction, ether (50 ml) was added. The mixture was washed with a saturated aqueous solution of sodium thiosulfate, water and saturated brine, and dried over anhydrous magnesium sulfate and concentrated under reduced pressure. The residue was purified by silica gel chromatography (ethyl acetate/n-hexane) to give 2-(2-phenoxyphenyl)-2-methoxyiminoacetamide (1.23 g, Yield: 91.0%, E/Z=23/77).

$^1$H-NMR (CDCl$_3$) δ ppm: 3.95(s,0.69H), 4.05(s,2.31H), 5.28–6.61(br.,m,2H), 6.84–7.59(m,9H).

EXAMPLE 43

Synthesis of 2-(2-methylphenoxymethyl)benzyl chloride

Acetonitrile (50 ml), potassium carbonate (13.82 g, 100 mmol) and α,α'-o-dichloroxylene (43.77 g, 250 mmol) were added to 2-cresol (5.41 g, 50 mmol). The mixture was heated under reflux for 3.5 hours. After completion of the reaction, the insoluble material was removed. The residue obtained after concentration under reduced pressure was purified by silica gel chromatography (ethyl acetate/n-hexane) to give 2-(2-methylphenoxymethyl)benzyl chloride (10.34 g, Yield: 83.8%) as a colorless oil.

$^1$H-NMR (CDCl$_3$) δ ppm: 2.26(s,3H), 4.74(s,2H), 5.21 (s,2H), 6.87–7.54(m,8H).

EXAMPLE 44

Synthesis of 2-(2-methylphenoxymethyl)benzyl cyanide

Aceton (5 ml), water (1 ml), 95% sodium cyanide (0.31 g, 6 mmol) and benzyltriethylammonium chloride (0.11 g, 0.5 mmol) were addd to 2-(2-methylphenoxymethyl)benzyl chloride (1.23 g, 5 mmol). The mixture was heated under reflux for 3 hours.

After completion of the reaction, toluene (100 ml) was added. The mixture was washed with brine (100 ml) twice, dried over anhydrous magnesium sulfate and concentrated under reduced pressure. The resulting residue was purified by silica gel chromatography (ethyl acetate/n-hexane) to give 2-(2-methylphenoxymethyl)benzyl cyanide (1.10 g, Yield: 92.7%) as a colorless oil.

$^1$H-NMR (CDCl$_3$) δ ppm: 2.23(s,3H), 3.89(s,2H), 5.08 (s,2H), 6.89–7.54(m,8H).

EXAMPLE 45

Synthesis of α-hydroxyimino-2-(2-methylphenoxymethyl)benzyl cyanide

Acetone (5 ml), 85% potassium hydroxide (powder)(0.40 g, 6 mmol) and butyl nitrite (0.62 g, 6 mmol) were added to 2-(2-methylphenoxymethyl)benzyl cyanide (1.19 g, 5 mmol). The mixture was stirred at room temperature for 1 hour. After completion of the reaction, 1N aqueous hydrochloric acid solution (100 ml) was added. The mixture was extracted with toluene (100 ml), dried over anhydrous magnesium sulfate and concentrated under reduced pressure. The resulting residue was purified by silica gel chromatography (ethyl acetate/n-hexane/chloroform) to give α-hydroxyimino-2-(2-methylphenoxymethyl)benzyl cyanide (1.23 g, Yield: 92.4%, E/Z=35/65) as colorless crystals.

A part of them was taken and separated into the E- and Z-isomers, and the physical properties were determined.

E-isomer:

mp 96.5°–98° C.

$^1$H-NMR (CDCl$_3$) δ ppm: 2.28(s,3H), 5.09(s,2H), 6.81–7.65(m,8H), 8.86(brs,1H).

Z-isomer:

mp 125.5°–127° C.

$^1$H-NMR (CDCl$_3$) δ ppm: 2.29(s,3H), 5.26(s,2H), 6.80–7.78(m,8H), 9.02(s,1H).

What is claimed is:
1. A process for producing a compound of the formula (II-1):

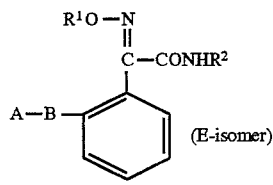

(II-1)

(E-isomer)

wherein A is hydrogen, alkyl, alkenyl, alkynyl, alkoxy, cycloalkyl, cycloalkenyl, optionally substituted phenyl or an optionally substituted heterocyclic group; B is —CH$_2$—, —O—, —S—, —CH(OH)—, —CO—, —NR$^3$— wherein R$^3$ is hydrogen or lower alkyl, —CH$_2$CH$_2$—, —CH=CH—, —C≡C—, —CH$_2$O—, —CH$_2$S—, —CH$_2$SO—, —OCH$_2$—, —SCH$_2$—, —SOCH$_2$— or epoxy; and R$^1$ and R$^2$ are identical or different and are hydrogen or lower alkyl; which comprises treating a compound of the formula (I-1):

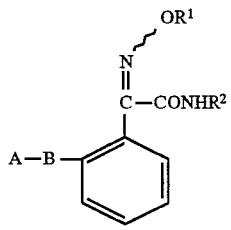

(I-1)

wherein ~ represents any configuration of the Z-isomer or a mixture of the E- and Z-isomers and other symbols are as defined above, with an acid or an acid addition salt of an organic base, provided that, when R$^2$ is lower alkyl, this process is carried out in the presence of a hydrocarbon, halogenated hydrocarbon, ether, ketone or mixed solvent thereof.

2. A process according to claim 1, wherein the acid is a hydrohalogenic acid, hydrogen halide or sulfonic acid.

3. A process according to claim 1, wherein the acid addition salt of an organic base is a hydrohalogenic acid addition salt of an organic base.

4. A process according to claim 1, wherein A is hydrogen, optionally substituted phenyl or an optionally substituted heterocyclic group; B is —CH$_2$—, —O—, —S—, —CH (OH)—, —CO—, —NR$^3$— wherein R$^3$ is hydrogen or lower alkyl, —CH$_2$CH$_2$—, —CH=CH—, —C≡C—, —CH$_2$O—, —CH$_2$S—, —CH$_2$SO—, —OCH$_2$—, —SCH$_2$—, —SOCH$_2$— or epoxy and the treatment is carried out in the presence of a hydrocarbon, halogenated hydrocarbon, ether, ketone or mixed solvent thereof.

5. A process according to claim 4, wherein the acid is a hydrohalogenic acid, hydrogen halide or sulfonic acid.

6. A process according to claim 4, wherein the acid addition salt of an organic base is a hydrohalogenic acid addition salt of an organic base.

7. A process for producing a compound of the formula (III):

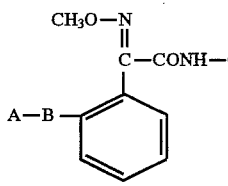

(III)

(E-isomer)

wherein A is hydrogen, alkyl, alkenyl, alkynyl, alkoxy, cycloalkyl, cycloalkenyl, optionally substituted phenyl or an optionally substituted heterocyclic group; and B is —CH$_2$—, —O—, —S—, —CH(OH)—, —CO—, —NR$^3$— wherein R$^3$ is hydrogen or lower alkyl, —CH$_2$CH$_2$—, —CH=CH—, —C≡C—, —CH$_2$O—, —CH$_2$S—, —CH$_2$SO—, —OCH$_2$—, —SCH$_2$—, —SOCH$_2$— or epoxy; which comprises treating a compound of the formula (I-2):

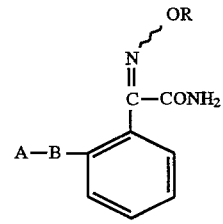

(I-2)

wherein R is hydrogen or methyl, ~ represents any configuration of the Z-isomer or a mixture of the E- and Z-isomers, and the other symbols are as defined above, with an acid or an acid addition salt of an organic base to obtain a compound of the formula (II-2):

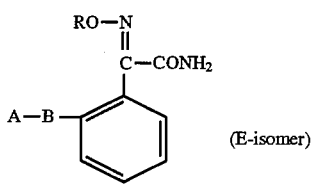 (II-2)

(E-isomer)

wherein each symbol is as defined above, and then methylating the compound of the formula (II-2).

8. A process for producing a compound of the formula (III):

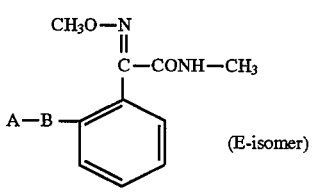 (III)

(E-isomer)

wherein each symbol is as defined in claim 7, which comprises hydrolyzing a compound of the formula (IV-1):

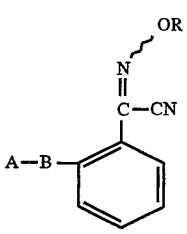 (IV-1)

wherein R is hydrogen or methyl and other symbols are as defined above, to obtain a compound of the formula (I-2):

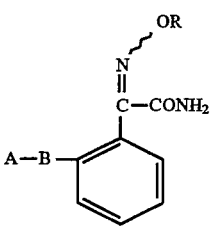 (I-2)

wherein each symbol is as defined above, treating the compound of the formula (I-2) with an acid or an acid addition salt of an organic base to obtain a compound of the formula (II-2):

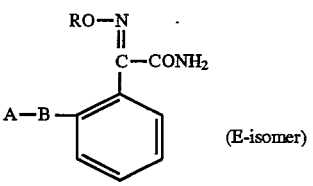 (II-2)

(E-isomer)

wherein each symbol is as defined above, and then methylating the compound of the formula (II-2).

9. A process for producing according to claim 8, wherein the compound of the formula (IV-1) is obtained by reacting a compound of the formula (VI-1):

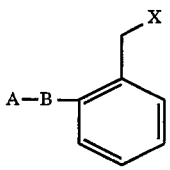 (VI-1)

wherein X is halogen and other symbols are as defined in claim 8, with an alkaline metal cyanide to obtain a compound of the formula (V-1):

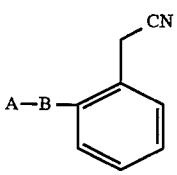 (V-1)

wherein each symbol is as defined above, forming an oxime from the compound of the formula (V-1), and then, if necessary, methylating the oxime.

10. A process according to claim 9, wherein a compound of the formula (XII):

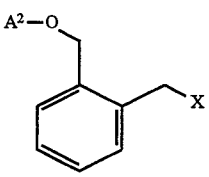 (XII)

wherein $A^2$ is alkyl, alkenyl, alkynyl, alkoxy, cycloalkyl, cycloalkenyl, optionally substituted phenyl or an optionally substituted heterocyclic group, and X is halogen, is obtained by reacting a compound of the formula (X):

$A^2$—OH (X)

wherein $A^2$ is as defined above, with a compound of the formula (XI):

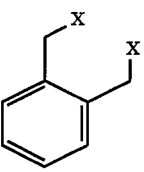 (XI)

wherein X is as defined above.

11. A process for producing a compound of the formula (XII):

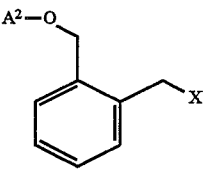 (XII)

wherein each symbol is as defined in claim 10, which comprises reacting a compound of the formula (X):

$A^2$—OH (X)

wherein $A^2$ is as defined above, with a compound of the formula (XI):

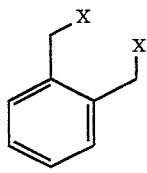 (XI)
wherein X is as defined above.
12. A process according to claim 11, wherein $A^2$ is substituted phenyl or an optionally substituted heterocyclic group.
13. A process according to claim 11, wherein the compound of the formula (XI) is used in an amount of 3 to 5 mol per mol of the compound of the formula (X).
* * * * *